(12) United States Patent
Sun et al.

(10) Patent No.: US 6,600,085 B2
(45) Date of Patent: Jul. 29, 2003

(54) ABSORBENT ARTICLE

(75) Inventors: Robert L. Sun, Succasunna, NJ (US); Shmuel Dabi, Highland Park, NJ (US)

(73) Assignee: Johnson & Johnson Consumer Products, Inc., Skillman, NJ (US)

( * ) Notice: Subject to any disclaimer, the term of this patent is extended or adjusted under 35 U.S.C. 154(b) by 0 days.

(21) Appl. No.: 09/740,742

(22) Filed: Dec. 19, 2000

(65) Prior Publication Data

US 2002/0115953 A1 Aug. 22, 2002

(51) Int. Cl.$^7$ ................................................. A61F 13/00
(52) U.S. Cl. ........................................ 602/56; 604/358
(58) Field of Search ......................... 604/304, 358–402; 442/181, 304; 428/175, 190, 193, 196; 602/41–43, 47–48, 44, 58, 59, 56

(56) References Cited

U.S. PATENT DOCUMENTS

| | | | |
|---|---|---|---|
| 3,929,135 A | | 12/1975 | Thompson |
| 3,989,867 A | | 11/1976 | Sisson |
| 4,324,246 A | | 4/1982 | Mullane et al. |
| 4,341,217 A | * | 7/1982 | Ferguson et al. ........ 604/385.1 |
| 4,342,314 A | | 8/1982 | Radel et al. |
| 4,463,045 A | | 7/1984 | Ahr et al. |
| 4,591,523 A | | 5/1986 | Thompson |
| 4,891,258 A | * | 1/1990 | Fahrenkrug ................. 428/138 |
| 4,977,892 A | * | 12/1990 | Ewall ........................... 602/52 |
| 4,990,144 A | | 2/1991 | Blott |
| 5,006,394 A | | 4/1991 | Baird |
| 5,505,720 A | * | 4/1996 | Walters et al. ............... 604/378 |
| 5,593,395 A | | 1/1997 | Martz |
| 5,614,283 A | * | 3/1997 | Potnis et al. ................. 428/131 |
| 5,632,731 A | | 5/1997 | Patel |
| 5,718,674 A | | 2/1998 | Penrose |
| 5,762,643 A | | 6/1998 | Ray et al. |
| 5,899,893 A | * | 5/1999 | Dyer et al. ................... 604/358 |
| 6,207,875 B1 | | 3/2001 | Lindqvist et al. |
| 6,232,521 B1 | * | 5/2001 | Bewick-Sonntag et al. . 604/378 |
| 6,277,104 B1 | | 8/2001 | Lasko et al. |

FOREIGN PATENT DOCUMENTS

| | | |
|---|---|---|
| EP | 0203822 A | 12/1986 |
| EP | 1040800 A1 | 4/2000 |
| WO | WO 9614038 A | 5/1996 |

OTHER PUBLICATIONS

PCT International Search Report, PCT/US01/45853.

* cited by examiner

Primary Examiner—Nicholas D. Lucchesi
Assistant Examiner—Lalita M Hamilton

(57) ABSTRACT

An absorbent article and a method for manufacturing an absorbent article are disclosed. The absorbent article is made from an inner core absorbent material, which is surrounded by an apertured film. The absorbent material is selected from rayon, cotton, wood pulp, polyester, polyamide, polyolefin, copolymers thereof, and combinations thereof. The absorbent article has a bottom layer, which is made of an apertured film oriented such that protuberances face the inside of the absorbent article. The absorbent article also has a top layer, which is made of an apertured film oriented such that the protuberances face the outside of the absorbent article. The absorbent article may be useful in various applications including sanitary protection and bandages.

23 Claims, 3 Drawing Sheets

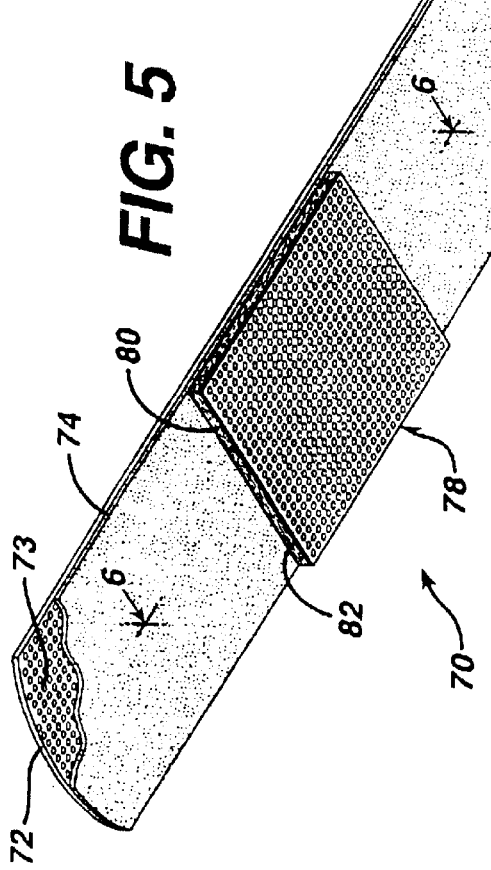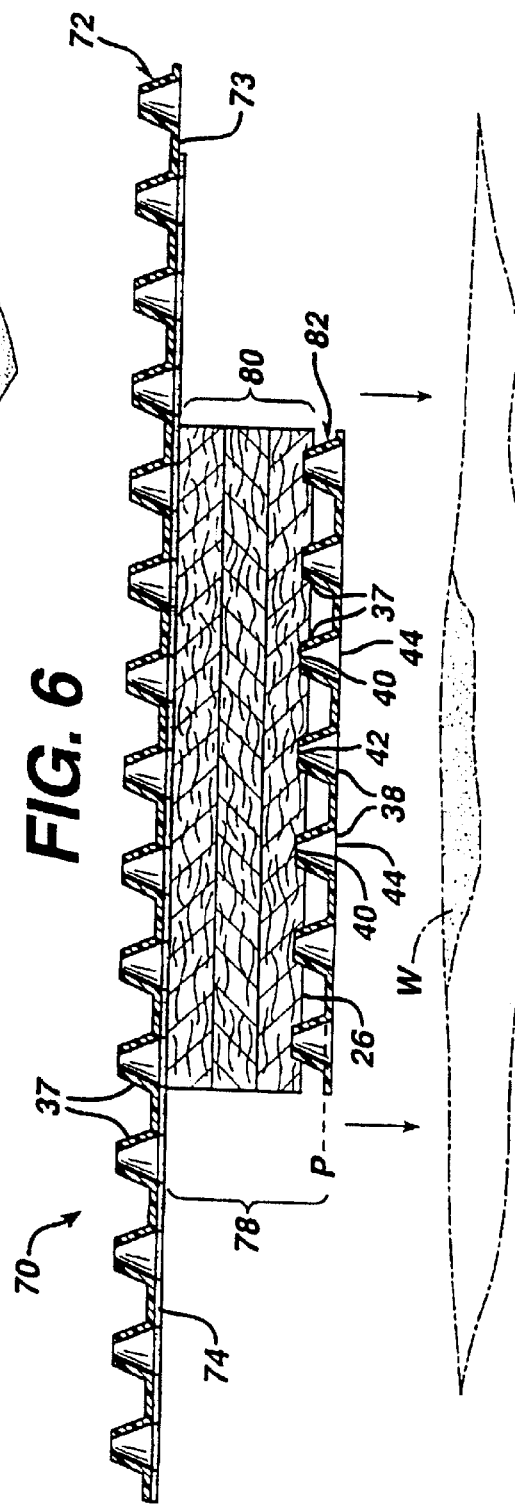

ABSORBENT ARTICLE

The present invention relates to absorbent articles. The absorbent articles comprise an absorbent core material which is covered by an apertured film. Absorbent articles of the invention are useful in various applications including sanitary protection products, diapers, and bandages.

Absorbent products such as sanitary napkins, disposable diapers and bandages are used to absorb body fluids such as menses, urine and wound exudate. These absorbent products generally require that the absorbent pad or absorbent article thereof be able to absorb a significant amount of body fluid. In some instances, the absorbent component must be capable of absorbing an amount of body fluid whose weight is greater than the weight of the absorbent material itself. It is also desirable that the body contacting surface of an absorbent product be dry, or relatively dry, even after the absorbent product has absorbed the body fluid, which it is designed to receive.

U.S. Pat. No. 3,929,135 discloses an absorptive structure comprising an absorbent material and an apertured film. The absorbent material may be, for example, comminuted wood pulp. The apertured film serves as a top sheet for the absorptive structure. The apertured film is smooth on one side, and has protuberances on the other side. The protuberances of the apertured film face the absorbent material thereby forming the absorptive structure.

U.S. Pat. No. 4,341,217 discloses a disposable absorbent article. The absorbent article has an absorbent core made of a material such as comminuted wood pulp. An apertured film encloses the absorbent core. The apertured film has protuberances which face both major surfaces of the absorbent core.

Despite the disclosure of the above-mentioned patents, there is a continuing need for an absorbent article with the ability to absorb a significant amount of fluid yet provide a dry feeling against the skin of the user after absorbing the fluid.

The present invention provides an absorbent article comprising an inner absorbent core material having a first major surface and a second major surface; a bottom layer; and a top layer. The bottom layer of the absorbent article comprises an apertured film having an open area and protuberances, and is oriented such that the protuberances face the inner absorbent core material. The top layer of the absorbent article comprises an apertured film having an open area and protuberances, and is oriented such that the protuberances face away from the inner absorbent core material.

Due to the design of the article of the invention, based on the orientation of the protuberances of the apertured film comprising the top and bottom layers, the article of the invention absorbs significant amounts of fluid. The bottom layer of the article of the invention faces the liquid to be absorbed. Fluids flow through the bottom layer of the absorbent article into the absorbent core. The absorbent core absorbs the fluids. The top layer of the absorbent article, owing to the specific orientation of its protuberances, tends to prevent liquids from entering into the absorbent article.

The absorbent core may be made from various materials including rayon fibers; natural fibers, such as, but not limited to, cotton fibers and wood pulp fibers; synthetic fibers, such as, but not limited to, polyester fibers, polyamide fibers, and polyolefin fibers, and combinations thereof. The fibers may be bicomponent fibers. For example, the bicomponent fibers may be in a sheath-core configuration in which the sheath comprises one polymer and the core comprises a different polymer. Bicomponent fibers having the other configurations, e.g., a side-by-side configuration, may also be used.

Preferably the fibers comprising the absorbent core are bonded at the points where they cross over and are in contact with each other. The bonding may be achieved, e.g., by heating the fibers so that they soften and fuse together at their crossover points. Alternatively, the fibers may be bonded by the use of an adhesive which can be applied by, e.g., spraying or gravure printing methods. Typically, the fibers are solid fibers; however, the fibers, or portions thereof, may be hollow fibers. Fibers having deniers ranging from about 3 to 10 may be advantageously used for the absorbent core. The basis weight for the absorbent core is not limited, but typically may range from 0.003 $g/cm^2$ to 0.015 $g/cm^2$.

In a preferred embodiment, the absorbent core comprises a nonwoven fabric made from bicomponent fibers which have been fusion-bonded using hot air. The bicomponent fibers are sheath-core fibers in which the sheath material comprises polyethylene and the core material comprises polyester. The denier of the sheath-core fibers is about 3. The nonwoven fabric has a basis weight of about 2 $oz/yd^2$.

The top layer and the bottom layer of the article of the invention are made from an apertured film having an open area and a plurality of protuberances. Such apertured films are disclosed in U.S. Pat. Nos. 3,929,135, 4,324,246, 4,342, 314, 4,463,045, and 5,006,394, the disclosure of each of which is hereby incorporated by reference.

Particularly useful apertured films include Vispore® apertured film supplied by Tredegar. Such apertured films include, but are not limited to, those available commercially under the designations Tredegar X-6799, Tredegar X-6845, Tredegar X-6923, Tredegar X-6944, and Tredegar X-6844. The film has a female side, which is smooth, and a male side, which is somewhat less smooth, due to the protuberances. The apertured films may be made from any polymeric material including, but not limited to, polyethylene, metallocene catalyzed polyethylene, polypropylene, and copolymers thereof, and ethylene vinyl acetate copolymers. An apertured film of one type may be used for the top layer, while a apertured film of another type may be used for the bottom layer. Usually, however, the same apertured film is used for both the bottom and top layers.

The open area of the apertured film comprising the bottom layer and the top layer of the absorbent article of the invention is defined as the area occupied by apertures. The open area for the top layer and the bottom layer of the article of the invention may range from 5 percent to 30 percent, preferably from 10 percent to 25 percent of the total area of the apertured film.

The bottom layer of the article of the invention may be treated with a hydrophilic surfactant including, but not limited to, laurate esters of sorbitol and sorbitol anhydrides condensed with ethylene oxide, such as polysorbate 20, polysorbate 40, polysorbate 60, and polysorbate 80; ethylene oxide/propylene oxide copolymers; octyl phenol ethoxylates; nonyl phenol ethoxylates; and ethoxylated alcohols. The term "treated" means that the bottom layer has had a hydrophillic surfactant incorporated therein during the polymerization process used to manufacture the polymeric resin from which the bottom layer is made, or the hydrophilic surfactant is incorporated with the polymer during the process by which the apertured film is made, or the bottom layer is coated with the hydrophillic surfactant after the bottom layer has been made.

The apertured film may, if desired, comprise Triclosan or a like anti-bacterial agent in an anti-bacterially effective amount. The apertured film comprises a smooth side and a side having protuberances. The bottom layer of the absorbent article of the invention is oriented such that the protuberances of the apertured film face the bonded absorbent core. The top layer of the article of the invention is oriented such that the protuberances of the apertured film face the outside of the absorbent article.

The bottom layer and the top layer of the absorbent article of the invention may be secured to the absorbent core material by means known in the art. For example, a suitable adhesive may be applied to the top of the absorbent core material, and the top layer may then be applied to the absorbent core. Then the bottom of the absorbent core may be coated with the adhesive and the bottom layer may be applied to the bottom of the absorbent core. Other means known in the art, e.g. ultrasonic bonding, may also be used.

The adhesives may be made from any polymerization process including solution or dispersion processes. The adhesives may be hot melt adhesives. Examples of suitable adhesives include, but are not limited to those based on styrenic block copolymers and tackifying resins such as HL-1491 from HB-Fuller Co. (St. Paul Minn.), H-2543 from ATO-Findley (Wawatausa, Wis.), and 34-5534 from National Starch & Chemical (Bridgewater, N.J.). Ethylene copolymers, including ethylene vinyl acetate copolymers, may also be useful. Suitable adhesives also include acrylic based, dextrin based, and urethane based adhesives as well as natural and synthetic elastomers. The adhesives may also include amorphous polyolefins including amorphous polypropylene, such as HL-1308 from H B Fuller or Rextac RT 2373 from Huntsman (Odesssa, Tex.). The adhesive may be compounded with Kraton® synthetic rubber and the like, or natural rubber with a tackifier and antioxidant process aids.

The adhesive can be applied in the molten stage, sprayed, or slot die coated. The spray can be applied by control coating, control weaving, control fiberization, meltblowing, flexo coating, screen printing, or other discontinuous coating methods.

The present invention also provides a method which utilizes the materials described above. The method includes: placing an apertured film having protuberances on a surface with the protuberances facing up; applying an adhesive to the top surface of an absorbent core material; placing the top surface of the absorbent core material on the apertured film; placing a second apertured film having protuberances on a surface with the protuberances facing up; applying an adhesive to the top surface of the second apertured film; and placing the bottom surface of the absorbent core material on the top surface of the second apertured film; whereby the absorbent article is formed.

The absorbent article of the invention may be made in any desired shape, including, but not limited to, round, oval, rectangular, square, and triangular. The size of the absorbent article of the invention will vary depending on the desired application.

Absorbent articles of the invention may be used as, or as components of, various products including, but not limited to, bandages, sanitary protection pads, diapers, and implements for carrying and/or dispensing anti-itch agents, acne treating agents, moisturizers, and the like. For bandages, the absorbent article of the invention may be square, rectangular, round, oval, or triangular in shape. The size of the bandage will depend on the shape of the bandage and the size of the wound meant to be covered by the bandage. Generally, a square bandage may range in size from 5 cm×5 cm to 15 cm×15 cm, preferably from 7.5 cm×7.5 cm to 12.5 cm×12.5 cm. The length of a rectangular bandage may range from 5 cm to 15 cm, preferably from 7.5 cm to 12.5 cm. The width of a rectangular bandage may range from 0.5 cm to 5 cm, preferably from 1 cm to 3 cm. A circular bandage may range in outer diameter from 5 cm to 20 cm, preferably from 7.5 cm to 17.5 cm, more preferably from 10 cm to 15 cm.

The thickness of the absorbent article of the invention will vary depending on the application, but generally may range from 0.25 mm to 5 mm, preferably 1 mm to 3 mm, more preferably 1 mm to 2 mm.

When the absorbent article of the invention is used as the wound contacting pad of a bandage, the bottom layer of the absorbent article is oriented toward the user's skin and serves as a wound release layer, meaning that the layer will not stick to the wound to which the bandage is applied. The bottom layer is made of the same apertured film described above. The top layer of the bandage is also made of the apertured film described above.

When used as the wound contacting pad of an adhesive bandage, the open area of the top layer of the absorbent article and the open area of the bottom layer of the absorbent article may be the same or may be different. In order to reduce the contact area of the bandage against the wound, the open area of the bottom layer of the absorbent article may range from 5 percent to 30 percent, preferably from 10 percent to 25 percent of the total area of the apertured film. The reduction in contact area against the wound reduces the wound release force. This results in a lower re-injury occurrence of the wound. The top layer of the absorbent article may have a smaller open area than the bottom layer of the bandage. The use of a top layer having a reduced open area tends to prevent undesirable escape of liquid from the inner absorbent core.

In one embodiment of an adhesive bandage, the absorbent article of the invention is secured, as by adhesive, to a backing comprising a polyethylene foam of any density, or conbinations of various density polyethylenes. The density of the foam may range from 0.008 $g/cm^3$ to 0.160 $g/cm^3$. The foam may be perforated or apertured. The size of the perforation or aperture may range from 0.01 mm to 5 mm. The total open area may range from 10 percent to 80 percent of the total foam area. The perforations or apertures may be made by extrusion, mechanical, hot-pinning or ultrasonic perforation. The thickness of the bandage may range from 1 mm to 3 mm.

BRIEF DESCRIPTION OF THE DRAWINGS

FIG. 5 is a schematic perspective of a second embodiment of an adhesive bandage in accordance with the teachings of the present invention; and FIG. 6 is a cross section taken along line 6—6 of FIG. 5.

Referring now to the accompanying drawngs, there is shown a first embodiment of an absorbent article in accordance with the teachings of the present invention. Referring to FIG. 1 and FIG. 2, absorbent article 20 comprises an absorbent core 24, a bottom layer 28 and a top layer 32. Absorbent core 24 has a first major, or upper, surface 25 and a second major, or lower, surface 26. Top layer 32 is secured, e.g., by adhesive, to upper surface 25 of absorbent core, while bottom layer 28 is secured, e.g., by adhesive, to lower surface 26 of the absorbent core. Those skilled in the art will understand that top and bottom layers 32, 28 can be secured to the absorbent core by means other than adhesive, for example, by heat-sealing. When adhesive is used, it is preferably applied in discontinuous fashion, for example, by spraying, screen printing, gravure printing or the like. Similarly, heat-sealing is preferably done in a discontinuous manner.

Absorbent core 24 may comprise a single fibrous web of any desired thickness. Alternatively, absorbent core 24 may comprise two or more such webs. As seen in FIG. 2, absorbent core 24 comprises three fibrous webs, 24a, 24b and 24c.

Figure 3:
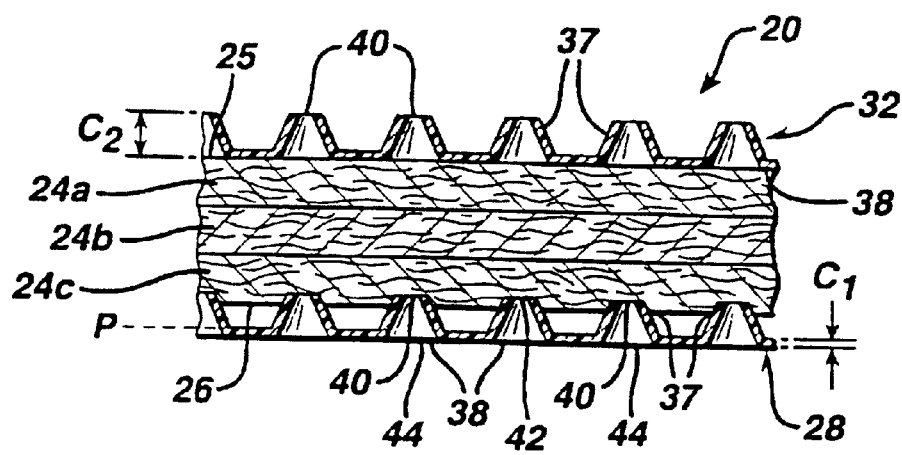
FIG. 3 is a greatly enlarged cross-sectional view of the absorbent article of FIG. 2 taken along line 3—3 of FIG. 1.

Bottom layer 28 preferably comprises an apertured plastic film which, as seen in FIG. 3, comprises a plurality of protuberances 37 each having a base 38 in the plane, P, of the film and an apex 40 remote therefrom. Apex 40 has an apex opening 42. Base 38 has a base opening 44. Base opening 44 is larger than apex opening 42. Bottom layer 28 is placed against lower surface 26 of absorbent core 24 such that apices 40 of its protuberances 37 come into contact with said lower surface of the absorbent core and the bases 38 of its protuberances 37 are remote from the lower surface of the absorbent core.

Top layer 32 of absorbent article 20 preferably comprises the same apertured plastic film as that used for bottom layer 28. However, the orientation of top layer 32 with respect to the absorbent core is different from the orientation of bottom layer 28. Specifically, as will be seen by reference to FIG. 3, top layer 32 is placed against upper surface 25 of absorbent core 24 such that apices 40 of its protuberances 37 are remote from the upper surface of the absorbent core and the bases 38 of its protuberances are disposed adjacent said upper surface of the absorbent core.

Each of top layer 32 and bottom layer 28 has a true caliper, C1, and an apparent caliper, C2. True caliper, C1, is the thickness of the material before protuberances 37 have been formed therein. Apparent caliper, C2, is the "in-use" thickness of the material after formation of protuberances 37 and is measured from base 38 to apex 40 of protuberance 37.

Figure 4:
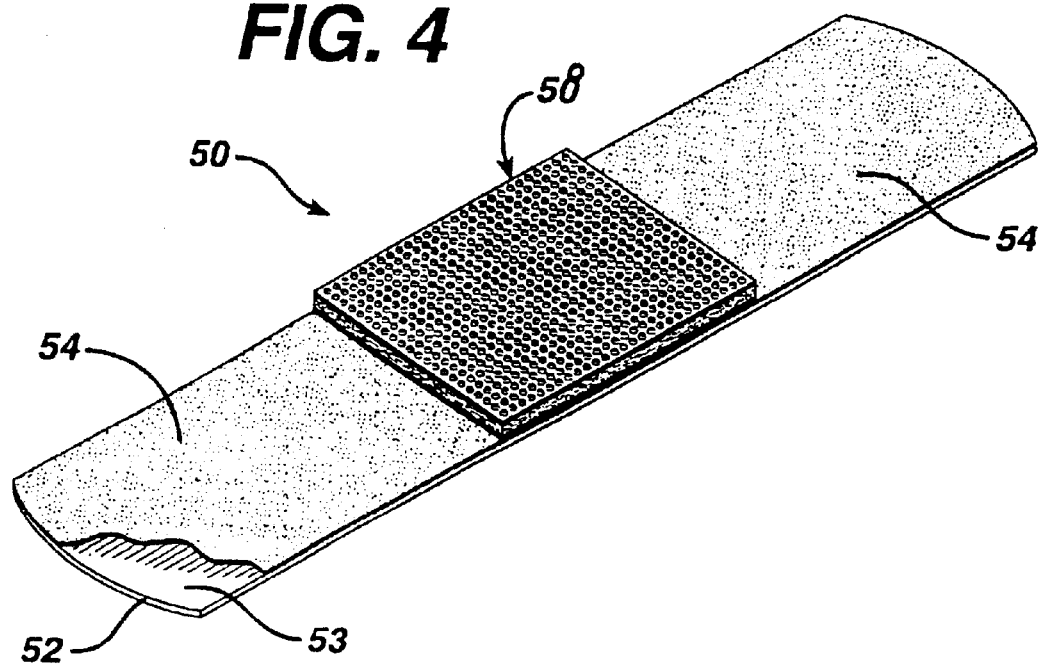
FIG. 4 is a perspective view of an adhesive bandage which uses the absorbent article of the invention as a wound contacting pad.

Referring now to FIG. 4, there is shown a perspective view of an adhesive bandage which uses the absorbent article of the present invention as its wound contacting pad. Adhesive bandage 50 comprises a backing 52 which may comprise, e.g., a foam or a thin plastic film comprising, e.g., polyvinyl chloride, polyethylene, polyurethane or the like. One major surface, 53, of backing 52 has an adhesive 54 (illustrated in FIG. 4 by stippling) applied thereto. Adhesive 54 may be any of the adhesives well known and used in the art and it may be applied to surface 53 using any well known adhesive application method.

Adhesive bandage 50 further comprises a wound contacting pad 58 which is secured to backing 52 by adhesive 54 in known manner. In the embodiment under discussion, wound contacting pad 58 is co-extensive in width with backing material 52 but is shorter in length than the backing. Wound contacting pad 58 is centered end-to-end of backing 52 as is known in the art.

Figure 1:
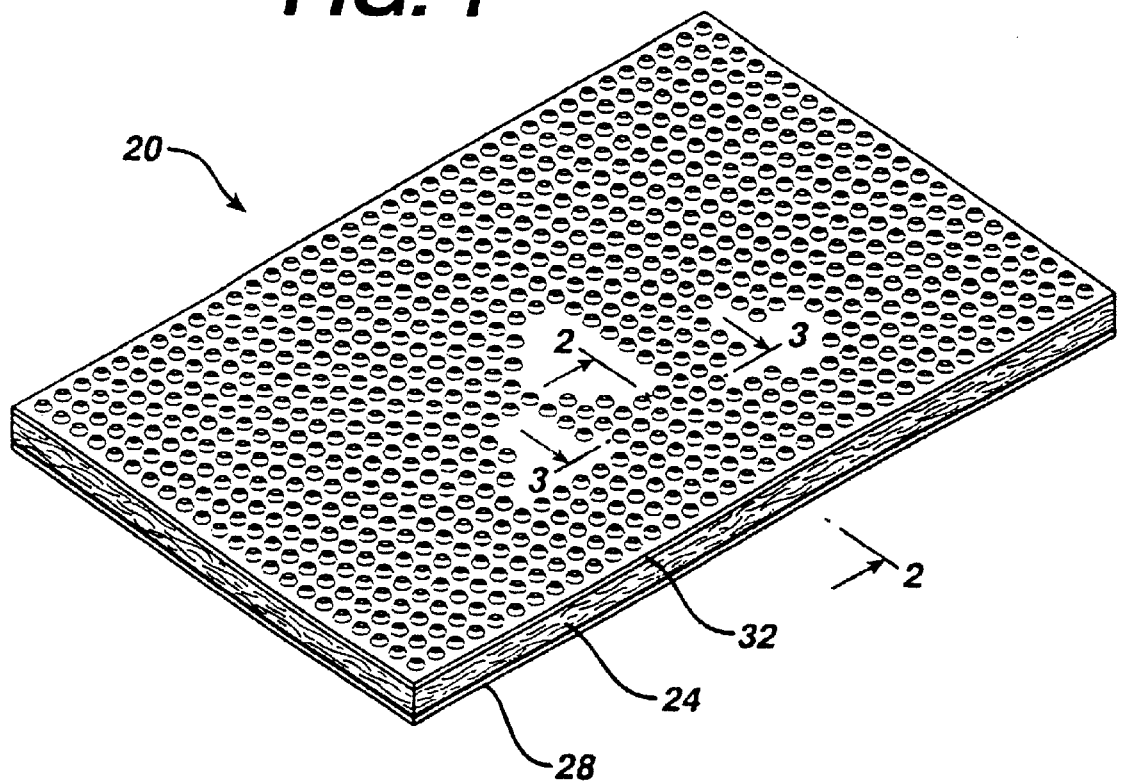
FIG. 1 is a perspective view of one embodiment of an absorbent article in accordance with the teachings of the present invention.
Figure 2:
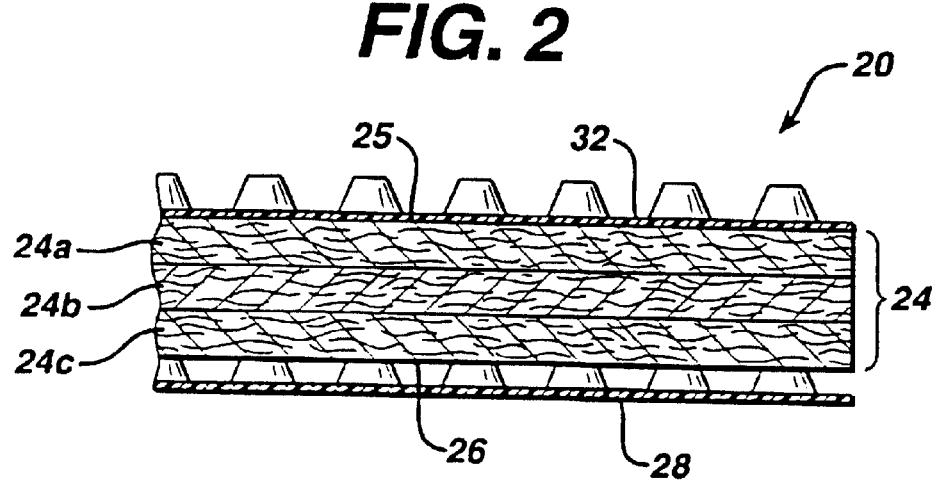
FIG. 2 is a cross-sectional view of the absorbent article of FIG. 1 taken along line 2—2 of FIG. 1.

Wound contacting pad 58 has the three-layer structure of absorbent article 20 illustrated in FIG. 1 and described hereinabove. Preferably, pad 58 is oriented on the adhesive coated surface of backing 52 so that protuberances 37 of top layer 32 (see FIG. 3) of absorbent article 20 come into contact with adhesive 54. As a result, that surface of bottom layer 28 which lies in plane P (see FIG. 3) faces away from adhesive coated surface 53 and, in use, contacts the wound which the user of the bandage desires to protect and/or treat.

Referring now to FIGS. 5 and 6 of the drawings, there is shown another embodiment of an adhesive bandage in accordance with the present invention. Adhesive bandage 70 comprises a backing 72 to one major surface 73 of which is applied an adhesive 74. Adhesive bandage 70 further comprises a wound contacting pad 78. In this embodiment, backing 72 comprises an apertured film of the kind discussed earlier herein, that is, the apertured film has an open area and protuberances 37. Wound contacting pad 78 is secured by underlying adhesive 74 to backing 72. Wound contacting pad 78 comprises a fibrous layer 80 and a cover layer 82. Wound contacting pad 78 is oriented on backing 72 so that its fibrous layer 80 comes into contact with adhesive 74. As a result, cover layer 82 faces away from the adhesive and, in ultimate use, comes into contact with the wound, W, which the user desires to protect or otherwise treat.

Cover layer 82, as was the case with backing layer 72, comprises an apertured film having an open area and a plurality of protuberances 37. As illustrated in FIG. 6, cover layer 82 is oriented on fibrous layer 80 such that its protuberances 37 face end come into contact with fibrous layer 80.

The following examples are intended to demonstrate the absorbent article of this invention. The examples should not be construed as limiting the scope of the invention.

EXAMPLE 1

Preparation of Absorbent Pads

Tredegar X-6799 apertured film was unwound, cut into a 20 cm×27 cm square, and placed with the protuberances up. Findley HM 3210 adhesive was applied to the entire top surface of a 20 cm×27 cm piece of PGI FB035C non-woven (a bonded bicomponent fiber). The non-woven pad was placed adhesive side down on top of the upwardly projecting protuberances of the apertured film. This was the source for the bandage pads. The source for the bandage pads was cut into 2.1 cm×1.2 cm bandage pads. A second piece of Tredegar X-6799 apertured film was unwound and cut into 7.6 cm×1.9 cm strips. The strips were placed with the protuberances facing down. Findley 3210 adhesive was applied to the upwardly facing surface of the strips. The bandage pads, prepared as described above, were placed non-woven side down onto the centers of the strips.

The process above was repeated substituting various apertured films for the Tredegar X-6799. Samples were prepared utilizing Tredegar X-6845, Tredegar X-6923, Tredegar X-6944, and Tredegar X-6844.

EXAMPLE 2

Wound Release Test

For bandages, it is important that the layer of the bandage that contacts the wound does not stick to the wound. Therefore, a wound release test is utilized to determine the quality of the bandage, in terms of not sticking to the wound. The absorbent pads prepared in Example 1 were tested and compared to a commercial product known for good wound release characteristics. The test was performed on female Yorkshire swine. On the day before the test, the animal was sedated and fur was removed from the animal's back and flank with electric clippers. A depilatory lotion was applied to the area. After 10 minutes, the lotion was removed with a metal spatula. The area was washed with mild soap and swabbed dry. The next day, the animal was sedated and a single row of twelve 2.5 cm×2.5 cm superficial wounds was created on each flank, parallel to the spinal column using a Brown Dermatome set at a depth of 0.08 cm. The wounds were wiped with a gauze sponge and the bandages were applied perpendicular to the spinal column. A stretch bandage was applied over the bandages to prevent movement or removal of the bandages.

Approximately 24 hours later, the animal was sedated. A Chatillon Digital Force Gauge Model DFGS2 with a chromatography clip attached to the bottom post of the unit by 5 cm of string was used to measure the bandage removal force. The stretch bandages were removed from the animal. The adhesive portions of the bandages were cut and removed from the animal, leaving only the pad on the wound. The chromatography clip was attached to the top or bottom edge of each bandage and the force gauge was zeroed. The gauge was lifted perpendicular to the plane of the wound surface until the string was taught. The gauge was pulled back at a steady even rate until the bandage was removed from the wound surface. The force required to remove each bandage (Mean Removal Force) was recorded (in grams). The results are shown in Table 1.

TABLE 1

| Sample | Mean Removal Force |
| --- | --- |
| Tredegar X-6799 | 110 |
| Tredegar X-6845 | 108 |
| Curad Telfa ®* | 286 |

*= Comparative

The data above demonstrate that the absorbent articles of this invention are useful as bandages and have improved wound release characteristics as compared with a commercial product known to have good wound release characteristics.

EXAMPLE 3

Absorbency Test

The potential applications for the articles of this invention all require that the article have high liquid absorbency. Therefore, the absorbency test was run on the absorbent pads prepared in Example 1 and a commercially available pad to determine how fast the article absorbs liquids, and how much liquid is retained in the article when pressure is applied (known as rewet). The test was performed by a modified IDANA 150.1-90 liquid strike-through time test. The results are shown in Table 2.

TABLE 2

| Sample | Penetration Rate (g/s) | Rewet (%) |
| --- | --- | --- |
| Tredegar X-6799 | 1.1 | 87 |
| Tredegar X-6844 | 1.0 | 87 |
| AET Pad Stock 3.702 NPI* | 0.54 | 94 |

The data above demonstrate the articles of this invention are useful in applications where high liquid absorbency is required, as they absorb more liquid than a commercial product known to have good liquid absorbency.

EXAMPLE 4

Moisture Evaporation Rate

While absorbent articles are required to have high liquid absorbency, they should also have high moisture evaporation rates. High moisture evaporation rates allow the liquid to pass from the upper surface of the absorbent article to the atmosphere. Therefore, the moisture evaporation rate test was run on the absorbent pads prepared in Example 1 and a commercially available pad to determine how fast liquids can pass from the absorbent article to the atmosphere. The test was performed by measuring the loss of water in the absorbent pads (by weight) and calculating the rate of loss (at 37° C.).

A microscope glass slide and adhesive bandage was weighed (W1), a syringe was used to add approximately 100 mg of deionized water on the pad, and the weight was checked (W2). The bandage was turned with the pad facing the glass and both edges of the pad areas were sealed with a light tape, such as Scotch® Tape. The weight of the slide, bandage, water and the tape was checked (W3). This was the T 0 point. The sample was placed in an oven at 37° C. and it's weight was rechecked at specified intervals until no changes were observed. The time table was 0, 5, 10, 20, 30, 60, and 90 minutes. Calculations: W2−W1 is the determination of the amount of water added and is used as the base (100%) for calculations at T 0 minutes. Weight differences between W3 at T 0 min and W3 at T×min will determine moisture loss in mg for the time tested. The results are expressed in % loss after the conversion from mg loss. The results are reported in Table 3.

TABLE 3

| | Weight Percent Lost | | |
| --- | --- | --- | --- |
| Time | Tredegar X-6923 | J & J Shear | 3M Comfort Strip |
| 0 | 0 | 0 | 0 |
| 5 | 25 | 11 | 17 |
| 10 | 43 | 23 | 42 |
| 20 | 77 | 40 | 57 |
| 30 | 104 | 54 | 75 |
| 60 | NT | 98 | 97.8 |
| 90 | NT | 100 | 99.6 |

The data above demonstrate that the absorbent articles of the present invention provide better moisture evaporation rates than a commercial product known for good moisture evaporation. Therefore, the articles of the present invention will be useful in terms of providing a dry surface against the skin of the user.

We claim:

1. An absorbent article comprising:
    an absorbent core material having a first major surface and a second major surface;
    a bottom layer; and
    a top layer;
    said bottom layer comprising an apertured film having an open area and a plurality of protuberances, the protuberances of said bottom layer facing and being in contact with said absorbent core,
    said top layer being in contact with said absorbent core and comprising an apertured film having an open area and a plurality of protuberances, the protuberances of said top layer facing away from said absorbent core.

2. The article of claim 1, wherein the absorbent core material is selected from rayon, cotton, wood pulp, polyester, polyamide, polyolefin, copolymers thereof, and combinations thereof.

3. The article of claim 1, wherein the absorbent core material comprises a bicomponent fiber.

4. The article of claim 1, wherein the absorbent core material is bonded.

5. The article of claim 1, wherein the apertured film of the bottom layer and the apertured film of the top layer comprise a polymeric material selected from the group consisting of polyethylene, metallocene catalyzed polyethylene, polypropylene, and copolymers thereof, and ethylene vinyl acetate copolymers.

6. The article of claim 1, wherein the article is a diaper.

7. The article of claim 1, wherein the article is a sanitary pad.

8. The article of claim 1, wherein the article is a bandage.

9. The article of claim 8, wherein the bottom layer of the article is treated with a hydrophilic surfactant.

10. The article of claim 9, wherein the hydrophilic surfactant is selected from the group consisting of laurate esters of sorbitol and sorbitol anhydrides condensed with ethylene oxide, ethylene oxide/propylene oxide copolymers, octyl phenol ethoxylates, nonyl phenol ethoxylates, and ethoxylated alcohols.

11. The article of claim 8, wherein the open area for the bottom layer of the bandage ranges from 5 percent to 30 percent of the total area of the apertured film.

12. The article of claim 11, wherein the open area for the bottom layer of the bandage ranges from 10 percent to 25 percent of the total area of the apertured film.

13. The article of claim 8, wherein the bottom layer is a polyethylene foam.

14. The article of claim 13, wherein the polyethylene foam has a density of from 0.008 g/cm$^3$ to 0.160 g/cm$^3$.

15. The article of claim 13, wherein the total open area ranges from 10 percent to 80 percent of the total foam area.

16. A method comprising:

placing an apertured film having protuberances on a surface with the protuberances facing up;

applying an adhesive to the top surface of an absorbent core material;

placing the top surface of the absorbent core material on the apertured film;

placing a second apertured film having protuberances on a surface with the protuberances facing up;

applying an adhesive to the top surface of the second apertured film; and placing the bottom surface of the absorbent core material on the top surface of the second apertured film;

wherein an absorbent article is formed.

17. The method of claim 16, wherein the absorbent article is a diaper.

18. The method of claim 16, wherein the absorbent article is a sanitary pad.

19. The method of claim 16, wherein the absorbent article is a bandage.

20. An adhesive bandage comprising:

a backing material having a length, a width, and a major surface; and a wound contacting pad;

said wound contacting pad being secured to said major surface of said backing material, said wound contacting pad comprising an absorbent core material having a first major surface and a second major surface;

a bottom layer; and a top layer, said bottom layer comprising an apertured film having an open area and a plurality of protuberances, the protuberances of said bottom layer facing and being in contact with said absorbent core, said top layer being in contact with said absorbent core and comprising an apertured film having an open area and a plurality of protuberances, the protuberances of said top layer facing away from said absorbent core.

21. The adhesive bandage of claim 20 wherein the width of said wound contacting pad is substantially the same as the width of said backing material and the length of said wound contacting pad is less than the length of said backing material.

22. The adhesive bandage of claim 21 wherein the length of said wound contacting pad is less than the length of said backing material and the width of said wound contacting layer is less than the width of said backing material.

23. The adhesive bandage of claim 21 wherein the backing material has an adhesive applied thereto, said wound contacting pad is secured to said backing material by said adhesive, and the perimeter of said wound contacting pad lies inwardly of the perimeter of said backing material, whereby a portion of the adhesive applied to said backing material lies outwardly of the perimeter of the wound contacting pad.

\* \* \* \* \*